United States Patent
Rason et al.

(10) Patent No.: US 10,306,909 B2
(45) Date of Patent: Jun. 4, 2019

(54) AMINO ACID BASED DIET WITH IMPROVED TASTE

(71) Applicant: N.V. Nutricia, Zoetermeer (NL)

(72) Inventors: Jonathan Rason, Utrecht (NL); Carole Springett, Utrecht (NL)

(73) Assignee: N.V. NUTRICIA, Zoetermeer (NL)

( * ) Notice: Subject to any disclaimer, the term of this patent is extended or adjusted under 35 U.S.C. 154(b) by 0 days.

(21) Appl. No.: 15/321,915

(22) PCT Filed: Jun. 30, 2015

(86) PCT No.: PCT/NL2015/050475
§ 371 (c)(1),
(2) Date: Dec. 23, 2016

(87) PCT Pub. No.: WO2016/003273
PCT Pub. Date: Jan. 7, 2016

(65) Prior Publication Data
US 2017/0143025 A1    May 25, 2017

(30) Foreign Application Priority Data
Jul. 1, 2014 (NL) ................. PCT/NL2014/050429

(51) Int. Cl.
| | |
|---|---|
| A23L 33/00 | (2016.01) |
| A61K 45/06 | (2006.01) |
| A61K 31/198 | (2006.01) |
| A61K 31/405 | (2006.01) |
| A61K 31/4172 | (2006.01) |
| A23L 2/52 | (2006.01) |
| A23L 33/12 | (2016.01) |
| A23L 33/16 | (2016.01) |
| A23L 33/175 | (2016.01) |
| A61K 9/00 | (2006.01) |
| A61K 31/715 | (2006.01) |
| A61K 38/16 | (2006.01) |

(52) U.S. Cl.
CPC ............. *A23L 33/40* (2016.08); *A23L 2/52* (2013.01); *A23L 33/12* (2016.08); *A23L 33/16* (2016.08); *A23L 33/175* (2016.08); *A61K 9/0053* (2013.01); *A61K 31/198* (2013.01); *A61K 31/405* (2013.01); *A61K 31/4172* (2013.01); *A61K 31/715* (2013.01); *A61K 38/16* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 5,411,757 A | 5/1995 | Buist et al. |
| 2004/0197401 A1 | 10/2004 | Calton et al. |
| 2005/0027006 A1* | 2/2005 | Matalon ............... A61K 31/195 514/561 |

FOREIGN PATENT DOCUMENTS

| | | |
|---|---|---|
| EP | 2 205 100 A1 | 7/2010 |
| WO | WO-2009/061603 A1 | 5/2009 |
| WO | WO 2010/144821 | * 12/2010 |

OTHER PUBLICATIONS

International Search Report issued in International Patent Application No. PCT/NL2015/050475 dated Aug. 20, 2015.

* cited by examiner

*Primary Examiner* — Elizabeth Gwartney
(74) *Attorney, Agent, or Firm* — Gilberto M. Villacorta; Sunit Talapatra; Foley & Lardner LLP

(57) ABSTRACT

The present invention is based on the finding that free amino acids can both negatively or positively influence overall taste of free amino acid-based enteral nutritional compositions, and the amino acids can thus be categorized. A striking balance of both categories of amino acids to arrive at amino acid-based nutritional composition with improved taste, yet not compromising the (regulatory) dietary restrictions on essential amino acids and conditionally essential amino acids.

19 Claims, No Drawings

AMINO ACID BASED DIET WITH IMPROVED TASTE

CROSS-REFERENCE TO RELATED APPLICATIONS

This application is the National Phase of International Patent Application No. PCT/NL2015/050475, filed Jun. 30, 2015, published on Jan. 7, 2016 as WO 2016/003273 A1, which claims priority to International Patent Application No. PCT/NL2014/050429, filed Jul. 1, 2014. The contents of which are herein incorporated by reference in their entirety.

The invention rests in the field of method of improving taste of free amino acid-based compositions, products thus obtained, and the use of such products for treating patients with metabolic diseases, particularly PKU patients.

BACKGROUND

Patients with inborn metabolic diseases are normally treated with a protein restricted diet. Such diet eliminates all foods originating from animal origin (milk, meet, fish, eggs, etc.). From birth on, these patients are therefore dependent of specifically designed medical foods.

The dietary management of many inborn metabolic diseases requires the absence of specific amino acids. For instance, phenylketonuria (PKU) patients require protein sources with as low as possible concentrations of phenylalanine. For many years enteral formulas have been developed that are based on free amino acids blended into a nutritional complete amino acid composition, but without the specific amino acid that the patient is unable to metabolize, e.g. phenylalanine in PKU patients. Other inborn metabolic diseases may require a different amino acid profile.

The free amino acid based formulas generally suffer from the problem that the taste is perceived as bad. Particularly when patients become older, palatability issues become more of a problem, which significantly impairs compliance with the product, which may lead to poor nutritional intakes or too high intakes of the amino acid that cannot be metabolized. Ultimately, this may affect neurological development of the patients.

U.S. Pat. No. 5,411,757 discloses food supplements to be added to low protein natural foods with up to 100% of certain unpalatable acidic L-amino acids: L-glutamic acid, L-aspartic acid, L-arginine, and L-methionine, replaced by their more palatable counterparts: L-glutamine, L-asparagine, L-citrulline, and L-cystine, respectively. In addition the supplement contains the mentioned amino acids in as low concentration as nutritionally possible in order not to affect the taste of the food to which the amino acids are added.

EP 2205100 relates to the same problem of bad taste in hydrolysed and amino acid based infant formulas and it describes a method for decreasing the bitterness of a protein-free infant formula. The method may comprise intermixing a protein equivalent source, a carbohydrate source, a fat source, vitamins, and minerals in a solution and adding sodium hydroxide or potassium hydroxide to adjust the pH of the formula to between 6.5 and 7.2. It is asserted that the addition has a positive effect on taste.

Taking taste concerns into account, many products are available on the market, such as Anamix (PKU), ANC Phenylade, PKU gel (Vitaflo/Nestle), XpheKid (MetaX), Phenex2 (Abbott) and Phenylfree 2 (Mead Johnson). All of these products are nevertheless troubled by a bitter or bad taste, at least to some extent, as shown in Table 1. In the art there is thus a need for improving the taste of these lines of nutritional products.

SUMMARY OF THE INVENTION

For long it has been known that nutritional compositions wherein the protein content contains significant amounts of free amino acids have a bad taste. In the art, many solutions to this problem have been advocated, such as coating of the free amino acids, use of small peptides instead of free amino acids, etc. The present inventors hypothesized that free amino acids can both negatively or positively influence overall taste of free amino acid-based enteral nutritional compositions, categorized the amino acids and found a striking balance of both categories of amino acids to arrive at amino acid-based nutritional composition with improved taste, yet not compromising the (regulatory) dietary restrictions on essential amino acids and conditionally essential amino acids.

The amino acid composition was assessed in view of the prior art disclosures, and a comparative study focussing on differences in taste appreciation was done with a composition according to the invention compared to a prior art product with an amino acid composition that is closest to the present invention, using a paired preference test as disclosed in example 2. It has been demonstrated that the composition according to the present invention is superior in taste compared to prior art compositions. Without wishing to be bound by any theory, the inventors believe that amino acids such as alanine, cystine, glutamine, glutamic acid, proline, serine, threonine and tyrosine contribute to the overall taste of the composition positively, compensating for any negative taste effects of other amino acids, such as arginine, aspartic acid, asparagine, histidine, isoleucine, leucine, lysine and methionine, tryptophan and valine. Based thereon, the inventors carefully designed blends of free amino acids which are low in essential amino acids leucine, lysine, valine, isoleucine, histidine, tryptophan and preferably high in methionine and cystine, threonine, glycine, and tyrosine, and with a taste and palatability that is appreciated as improved over conventional amino acid-based formulas.

DETAILED DESCRIPTION

A first aspect of the invention pertains to an enteral nutritional composition with improved taste comprising as free amino acids 0-10 g phenylalanine, 4-8 g valine, 2.5-12 g threonine, 0.7-3 g tryptophan, 2.5-6 g isoleucine, 2-4 g methionine, 6.5-8.5 g leucine, 5-7 g lysine, and 2-3 g histidine, expressed per 100 g protein equivalent in the composition. The levels of isoleucine and threonine are preferably 3-6 g and 3-12 g, expressed per 100 g protein equivalent in the composition, respectively. When expressed directly in weight of free amino acids, the invention preferably pertains to an enteral nutritional composition with improved taste comprising as free amino acid 0-10 g phenylalanine, 4-8 g valine, 2.5-11 g threonine, 0.7-3 g tryptophan, 2.5-6 g isoleucine, 1.5-4 g methionine, 6.5-8.5 g leucine, 3-6 g lysine, and 1.5-3 g histidine, expressed per 100 g free amino acids in the composition. The levels of isoleucine and threonine are preferably 3-6 g and 3-11 g, per 100 g free amino acids in the composition, respectively.

More preferably, the composition comprises as free amino acid 0-10 g phenylalanine, 4-6.5 g valine, 8-12 g threonine, 0.7-3 g tryptophan, 3.5-6 g isoleucine, 2-4 g methionine, 6.5-8.5 g leucine, 5-7 g lysine, and 2-3 g histidine, expressed per 100 g protein equivalent in the composition. When expressed directly in weight of free amino acids, the invention preferably pertains to an enteral nutritional composition with improved taste comprising as free amino acid 0-10 g phenylalanine, 4-6.5 g valine, 7-11 g threonine, 0.7-3 g tryptophan, 3.5-6 g isoleucine, 1.5-4 g methionine, 6.5-8.5 g leucine, 3-6 g lysine, and 1.5-3 g histidine, expressed per 100 g free amino acids in the composition.

The composition preferably comprises as free amino acids 0-2 g phenylalanine, 5-8 g valine, 2.5-10 g threonine, 1-2 g tryptophan, 2.5-6 g isoleucine, 2-3 g methionine, 7.5-8.5 g leucine, 6-7 g lysine, and 2-3 g histidine, per 100 g protein equivalent in the composition, even more preferably the composition comprises as free amino acids 0-2 g phenylalanine, 5-6.5 g valine, 8.5-10 g threonine, 1-2 g tryptophan, 4-6 g isoleucine, 2-3 g methionine, 7.5-8.5 g leucine, 6-7 g lysine, and 2-3 g histidine, per 100 g protein equivalent in the composition. When expressed directly in weight of free amino acids, the composition may preferably comprise as free amino acids 0-2 g phenylalanine, 4-8 g valine, 2.5-9 g threonine, 0.7-1.5 g tryptophan, 2.5-7.5 g isoleucine, 1.5-2.5 g methionine, 6.5-7.5 g leucine, 3.5-5 g lysine, and 1.5-2.5 g histidine, per 100 g free amino acids in the composition, and even more preferably the composition comprises, as free amino acids, 0-2 g phenylalanine, 4-6 g valine, 7.5-9 g threonine, 0.7-1.5 g tryptophan, 6.5-7.5 g isoleucine, 1.5-2.5 g methionine, 6.5-7.5 g leucine, 3.5-5 g lysine, and 1.5-2.5 g histidine, per 100 g free amino acids in the composition.

The proteinaceous matter in the composition preferably comprises at least 80 wt %, more preferably 85 wt %, even more preferably at least 90 wt %, most preferably at least 95 wt % free amino acids.

The composition is particularly suited for PKU patients, in which case it is preferred that the composition comprises substantially no phenylalanine as free amino acid, preferably less than 0.5 g phenylalanine per 100 g free amino acids, more preferably less than 0.1 g phenylalanine per 100 g free amino acids, most preferably no or no detectable amounts of phenylalanine.

The present invention particularly relates to nutritional compositions comprising free amino acids at least as main protein equivalent. In general, at least 80 wt. % of the proteinaceous matter comprised in the composition is formed from free amino acids, more preferably at least 85 wt %, more preferably at least 90 wt % of the proteinaceous matter comprised in the composition. However, it is preferred that the proteinaceous material contains at least 95 wt % amino acids, based on all proteinaceous matter. The terms 'protein equivalent' and 'proteinaceous material' in the context of the invention are used interchangeably. Proteinaceous" material is understood to comprise mainly free amino acids. It may further include di- or tripeptides, and a non-allergenic protein source such as glycomacropeptide in those cases where the supplement is to be consumed by patients suffering from PKU. Glycomacropeptide does not comprise phenylalanine and as such can be used in dietary management of PKU sufferers. The amino acids present in the dietetic supplement of the invention may be present in any suitable form, especially in any form appropriate for foodstuffs. Illustratively the amino acids may be present as equivalents, e.g. in the form of salts, hydrochlorides, hydrates, acetates and maleates etc. In the most preferred embodiment the proteinaceous material consists of free amino acids.

From dietary management perspective, for adults and children over the age of 2 years, the list of essential or conditionally essential amino acids present in the composition preferably consists of amino acids selected from the group consisting of Cys, His, Ile, Leu, Lys, Met, Thr, Trp, Tyr, Phe and Val. For infants under the age of 2 years, Arg, Cys, Gln, His, Ile, Leu, Lys, Met, Thr, Trp, Tyr, Phe and Val are considered to be essential or conditionally essential amino acids which are preferably included in the composition. The essential amino acids preferably form 50-90 wt %, more preferably 60-80 wt % of all proteinaceous material present in the composition.

In addition, the amino acids arginine, cysteine (and/or cystine), glycine, glutamine, histidine, proline, serine and tyrosine are considered conditionally essential, meaning they are not normally required in the diet, but must be supplied exogenously to specific individuals that do not synthesize it in adequate amounts. The composition may further contain one or more of the non-essential amino acids Ala, Asp. These non-essential or conditionally essential amino acids preferably make up for a total amount of 10-50 wt %, more preferably 20-40 wt % of free amino acids, based on all proteinaceous material in the composition. As will be understood by the skilled person, one or more amino acids may be omitted, in view of a subject's medical condition, e.g. in case the subject to be treated with a composition according to the invention has PKU the amino acid Phe is omitted.

In a preferred embodiment, the sum of the amount of free amino acids selected from a first group A consisting of alanine, cysteine (preferably as cystine), glutamine, glutamic acid, proline, serine, threonine and tyrosine is at least 50 wt %, more preferably ranging between 55 and 80 wt %, more preferably between 60 and 75 wt %, most preferably between 65 and 70 wt %, based on the total free amino acids in the composition. In a preferred embodiment, all of these free amino acids categorized in group A are present in the composition.

In a preferred embodiment, the sum of the amount of free amino acids selected from a second group B consisting of arginine, aspartic acid, asparagine, histidine, isoleucine, leucine, lysine methionine, tryptophan and valine is less than 45 wt %, more preferably ranging between 20 and 45 wt %, more preferably between 25 and 40 wt %, most preferably between 30 and 35 wt %, based on the total sum of free amino acids in the composition. In a preferred embodiment, all of these free amino acids categorized in group B are present in the composition.

Additionally or alternatively, the weight ratio of the sum of the free amino acids selected from group A consisting of alanine, cysteine (preferably as cystine), glutamine, glutamic acid, proline, serine, threonine and tyrosine to the sum of the free amino acids selected from group B consisting of arginine, aspartic acid, asparagine, histidine, isoleucine, leucine, lysine methionine, tryptophan and valine in the composition ranges between 60:40 and 75:25, more preferably 65:35 and 70:30, most preferably around 2:1. In a preferred embodiment, all of these amino acids from Group A and Group B are present in the composition.

In one embodiment, the composition further comprises 6-8 g, preferably 6.5-7.5 g cystine, 14-18 g glycine, and 8.5-10.5 g tyrosine as free amino acids, expressed per 100 g protein equivalent in the composition. Alternatively, the composition further comprises 5-7, preferably 5.5-6.5 g cystine, 10-14 g glycine, 8-10 g tyrosine as free amino acids, per 100 g free amino acids in the composition.

Although generally appreciated as a sweet tasting amino acid, in one embodiment, the composition comprises less than 5 g serine, preferably 4-5 g serine, per 100 g protein equivalent, or less than 4, preferably 2.5-4 g serine, per 100 g free amino acids.

Additionally, the composition preferably comprises cysteine (and/or cystine), tyrosine, and arginine, which are amino acids which are required by infants and growing children.

An example would be the disease phenylketonuria (PKU). Individuals living with PKU must keep their intake of phenylalanine extremely low to prevent mental retardation and other metabolic complications. However, they cannot synthesize tyrosine from phenylalanine, so tyrosine becomes essential in the diet of PKU patients.

In particular, in accordance with the invention it is considered that the amino acids tyrosine and cysteine are conditionally indispensible amino acids for subjects suffering from specific metabolic disorders, depending on specific nutritional treatments, and therefore preferably added to the nutritional composition of the invention, particularly when the composition is intended being a complete nutritional composition that should contain all ingredients needed for a healthy diet.

In a preferred embodiment, the composition comprises about 17 g alanine, about 6.5 g arginine, about 1.5 g of the sum of aspartic acid and asparagine, about 7.0 g cystine, about 12 g of the sum of glutamic acid and glutamine, about 16.5 g glycine, about 2.5 g histidine, about 5.0 g isoleucine, about 8.0 g leucine, about 6.5 g lysine, about 2.5 g methionine, about 8.0 g proline, about 4.5 g serine, about 9.0 g threonine, about 1.5 g tryptophan, about 9.5 g tyrosine and about 6.0 g valine, expressed per 100 g protein equivalent, including a 20% weight variation, more preferably a 10% weight variation, most preferably a 5% weight variation in the amount of the individual amino acids, independently. Preferably, the above recipe allows for a maximum deviation of ±0.2, more preferably ±0.1 g in the amounts of free amino acids independently, thus encompassed in the terminology 'about' as used here above. The term 'protein equivalent' is an art-recognized term to express the amounts of the free amino acids as the amount of amino acids as if it was part of a protein, i.e. the weight value of amino acids is understood as the protein equivalent weight value, unless otherwise specified. Individual amino acids have their own conversion factor. On average, one gram amino acids corresponds to 0.833 g protein equivalent.

Alternatively throughout the application the amounts 'per 100 g protein equivalent' can be expressed as gram free amino acid per 100 g free amino acids using the WHO conversion factor of each amino acid. Expressed in this way a preferred embodiment according to the invention comprises about 13 g alanine, about 6 g arginine, about 1 g of the sum of aspartic acid and asparagine, about 6 g cystine, about 10 g of the sum of glutamic acid and glutamine, about 12 g glycine, about 2 g histidine, about 4 g isoleucine, about 7 g leucine, about 4 g lysine, about 2 g methionine, about 7 g proline, about 3 g serine, about 8 g threonine, about 1 g tryptophan, about 9 g tyrosine, and about 5 g valine per 100 g free amino acids in the composition, including a 20% weight variation, more preferably a 10% weight variation, most preferably a 5% weight variation in the amount of the individual amino acids, independently (provided that the sum of all amino acids makes up for the total of 100 g free amino acids).

Preferably, the above recipe allows for a maximum deviation of ±0.2, more preferably ±0.1 g in the amounts of free amino acids independently, thus encompassed in the terminology 'about' as used here above.

Unless specified otherwise, the numbers in the two preceding paragraphs could thus be used to recalculate the numbers and amounts of free amino acids in terms of protein equivalent throughout the application without changing any subject-matter.

'Cystine'—being a dimer of cysteine—is counted as its corresponding free amino acid, and its contribution is thus calculated in terms of the amount of corresponding free amino acid cysteine. This product is particularly suited for use in treating or feeding PKU patients, or methods for treating or feeding PKU patients.

In one embodiment of the invention, part of the amino acids are replaced glycomacropeptide (GMP) which is naturally about devoid of phenylalanine and thus suited for administration to PKU patients. The composition may comprise up to 75 wt % GMP, based on the weight of all proteinaceous matter, the remainder of the proteinaceous matter being formed from free amino acids to the extent that the amino acid profile is as defined here above, albeit it calculated in terms of all amino acids either in free form or part of GMP altogether. The advantage of GMP is that the total level of free amino acids can be decreased in the total composition further improving taste of the product.

Use of the Composition According to the Present Invention

The composition according to the present invention is preferably used for the nutritional management of a subject, in particular a human that has a disorder selected from the group consisting of phenylketonuria, homocystinuria, maple syrup urine disease, tyrosinaemia, propionic acidaemia, methylmalonic acidaemia, isovaleric acidaemia, urea cycle disorders and glutaric aciduria. Worded differently, the invention also pertains to the use of the composition according to the invention in the manufacture of a product for the nutritional or dietary management of a subject as defined here above.

Preferably the composition according to the invention is for use in the improvement of nutritional status, the improvement of gut health, or for stimulation of catch-up growth in children suffering from metabolic diseases selected from the group consisting of phenylketonuria, homocystinuria, maple syrup urine disease, tyrosinaemia, propionic acidaemia, methylmalonic acidaemia, isovaleric acidaemia, urea cycle disorders and glutaric aciduria. Worded differently, the invention also pertains to the use of the composition according to the invention in the manufacture of a product for improvement of nutritional status, the improvement of gut health, or for stimulation of catch-up growth in children suffering from metabolic diseases selected from the group consisting of phenylketonuria, homocystinuria, maple syrup urine disease, tyrosinaemia, propionic acidaemia, methylmalonic acidaemia, isovaleric acidaemia, urea cycle disorders and glutaric aciduria.

A composition according to the invention may in particular be suited for use in preventing, treating or reducing the risk of developing a neurological disorder in a subject having a metabolic disorder, associated with the subject is not being capable of adequately metabolizing a specific amino acid (e.g. a subject having PKU) or a metabolite of the amino acid. The composition may in particular be used to avoid or reduce the risk of the occurrence of elevated plasma levels of an amino acid or metabolite thereof that would cause or contribute to a neurological problem, or to treat a subject having an elevated plasma level of said amino acid or metabolite thereof, in order to decreased the elevated plasma level of the amino acid or metabolite thereof. For instance, it is established that increased levels of phenylalanine may cause brain damage in PKU patients. Worded differently, the invention also pertains to the use of the composition according to the invention in the manufacture of a product for preventing, treating or reducing the risk of developing a neurological disorder as defined here above.

Alternatively, a composition according to the invention is suitable for use in the dietary management of food allergy in infants and children. These infants cannot tolerate mother's milk, standard infant formula or even hypo-allergenic infant formula (with hydrolysed protein). The inventors believe that a taste closer to that of standard infant milk formula is beneficial for the acceptance of the amino acid-based non-allergic infant formula. A composition according to the present invention significantly decreases the taste difference with standard infant formula, In the context of the invention, 'treatment' includes in particular nutritional/dietary management. For the present invention this means providing nutrition with a dedicated protein source comprising all necessary amino acids and without the amino acid that cannot be metabolised adequately to a harmless metabolite by a subject for which the composition is intended.

Use of a composition according to the invention generally comprises administration of an effective amount of the composition to a subject in need thereof. The effective amount can generally be based on the protein needs of a subject, for instance dependent on age and gender, and it common general knowledge for the skilled person to establish effective amounts of amino acids for the intended purpose.

The composition may in principle be administered in any way, preferably enteral administration. Preferably it is ingested orally or fed into the gastro-intestinal tract by tube feeding. Oral administration is most preferred. Within the context of the present invention, "enteral" means any form of administration that involves any part of the gastrointestinal tract, i.e. by mouth (orally), by gastric feeding tube, duodenal feeding tube, or gastrostomy, and rectally, in particular by mouth (orally). Hence, when referring to an enteral composition, this means that the composition is suitable for enteral administration.

With the "dietary management" of an individual is meant the administration of nutritional components to an individual, in such a way that not only the endogenous concentrations of nutritional components are influenced, but that also a health-beneficial effect is obtained.

In one aspect, the invention pertains to a method for enterally (preferably orally) feeding a subject the composition according to the invention. The invention also pertains to a method for dietary or nutritional management or treatment of a subject by enteral administration (preferably oral administration) of a composition according to the invention. The 'subject' is preferably a human suffering from a metabolic disorder selected from the group consisting of phenylketonuria, homocystinuria, maple syrup urine disease, tyrosinaemia, propionic acidaemia, methylmalonic acidaemia, isovaleric acidaemia, urea cycle disorders and glutaric aciduria, particularly PKU. The composition and particularly its proteinaceous content as used in these methods has been specified throughout the specification.

Food Formats

The composition according to the invention may be used as a protein substitute in solid or semi-solid foods, for instance sprinkled on crisps, mashed in potato etc. Alternatively, new food items may be prepared by incorporating the nutritional composition as a supplement therein. Since the nutritional supplement provided by the invention is neutral in terms of taste and smell, its incorporation in foods does not require additional flavourings for compensation.

While the nutritional composition can be used as a protein supplement, it is preferably a complete nutrition, further comprising fat, carbohydrates and protein equivalents, and micronutrients vitamins, trace elements and minerals. The composition preferably comprises between 15-45 en % fat, 10-70 en % digestible carbohydrates, 10-35 en % proteinaceous material, and optionally 5-15 en % fermentable dietary fiber, wherein 'en %' stands for energy percent and reflects the caloric contribution to the total caloric content of the nutritional product.

The product can be in any form or format such as a dry powder, liquid, gelled product, pudding, nutritional bar, dry and liquid soups, sports drink, etc.

In accordance with the present invention, liquid products are typically products that are pourable (at 20° C.), in particular pourable from an opened container in which they are contained, or that can be withdrawn from a container by sucking (by a person consuming the liquid) through a straw. In particular, the product of the invention is in liquid or pourable form and exhibits a viscosity of less than 2000 mPa·s at 20° C. and a shear rate of 100 s−1. Within the context of the invention, the viscosity can be measured using an Anton Paar Physica MCR301 rheometer with a CP50-1/PC cone (diameter 50 mm, 1° difference between middle and outside). In particular for a liquid product that is intended for administration by drinking, or via a straw or tube, the viscosity preferably is 400 mPa·s or less, more preferably 200 mPa·s or less, most preferably between 15 and 200 mPa·s.

A gelled product is a (previously) liquid product that has been thickened or gelled using specific thickeners such that it cannot be poured anymore without first disturbing the gel network (e.g. a network of polymer chains that form a three dimensional network). Gelled products according to the invention can for instance be administered by spooning. Suitable thickeners are xanthan gum, carrageenan, starch, and pectin, or mixtures thereof.

In one embodiment, the composition is sterilized, preferably heat-sterilized, and/or pasteurized.

In one embodiment of the present invention, the composition according to the invention is packaged. The packaging may have any suitable form, for example a block-shaped carton, e.g. to be emptied with a straw, a carton or plastic beaker with removable cover.

Indigestible Carbohydrates.

Indigestible carbohydrates have a dual purpose in the present invention. Indigestible carbohydrates are present for their nutritional benefits and because of their effect on the product stability and taste. The inventors believe that the addition of indigestible carbohydrate improves the taste and mouth feel of the product. This is important for improving the compliance of the product.

Preferably the composition comprises pectin as gelatinizer, and Locus bean gum, gellan gum, alginate, carrageenan, xanthan, guar gum or mixtures thereof as stabilizer. Preferably xanthan, guar gum or both are used as stabilizer. In particular pectin has the advantage of increasing the viscosity only after the pasteurization or sterilization heating step and not before cooling down the product. Therefore pipes needed for processing the product are not clogged by the product. This is contrary to many other thickeners that increase viscosity even before heating or during heating, and thereby complicating processing. In addition to that, pectin has excellent gelling characteristics in free amino acid based product and improves the taste. Therefore, in a preferred embodiment the composition of the invention comprises pectin. For a positive effect on the taste and mouth feel of the product, the concentration of pectin should not be too low or too high, preferably between 0.3 and 1.5 g/100 ml.

The inventors believe that for adequate feeding of pediatric patients it is very important to solve the constipation problem associated with amino acid based formula in order to improve compliance of the diet. Therefore the present composition according to the invention preferably the composition comprises added dietary fiber in sufficient amount, preferably between 1-4 g/100 kcal product. This would result in a daily fiber intake of about 20-30 g as recommended. Dietary fibers are preferably selected from soluble fibers Galactooligosaccharides, Fructooligosaccharides and fructopolysaccharides (inulin); and insoluble fibers cellulose, resistant starch and soy polysaccharides. Soy polysaccharides are fermentable while cellulose and resistant starch are non-fermentable fibers. Other fibers and gums may also be present.

Fermentable dietary fibers contribute to the caloric content of the composition with 2 kcal per gram fermentable dietary fiber.

Digestible Carbohydrates

The product according to the present invention preferably comprises digestible carbohydrates. Due to the fact that the product already comprises free amino acids the osmolarity of the product is already relatively high and should preferably not be increased too much by the carbohydrates. In order to do so, the carbohydrates are preferably in polymeric form with an average degree of polymerization of above 12. Starch or polydextrose are preferably used. Relative small amounts of mono or disaccharides can be added for taste reasons, e.g. by using glucose syrup as ingredient. Preferably such mono and disaccharides are replaced by artificial sweeteners such as saccharine, cyclamate, aspartame (not for Phe free products), stevia, sucralose, neotame, acesulfame potassium, and saccharin since these sweeteners will have a similar taste effect while not significantly affecting the osmolarity of the composition.

Fat

Fat is a concentrated form of energy that contributes little to formula osmolality.

As explained above, this is important for amino acid-based compositions. In addition, it carries fat soluble vitamins and is a source of essential fatty acids. Preferably fat is present between 0 and 50% of the total energy of the composition. In a liquid or gelled composition, the fat is preferably present in a concentration between 0 and 15 g/100 ml, even more preferably between 0.10 and 10 g/100 ml and most preferably between 0.30 and 5 g/100 ml.

The type of fat is merely restricted in that it should be food quality. The fat may either be an animal fat or a vegetable fat or a combination of both. The term fat as used herein includes fatty oils (fats that are liquid at room temperature). Major examples of fats are triglycerides and phospholipids. The fat typically is a source of fatty acids. The fat may include a source of medium chain fatty acids (mainly 8 to 10 carbon atoms long), such as medium chain triglycerides (MCT), a source of long chain fatty acids (mainly at least 18 carbon atoms long), such as poly-unsaturated fatty acids (PUFA's) as omega-3 and omega-6 fatty acids, including EPA, DHA and long chain triglycerides (LCT), and phospholipid-bound fatty acids such as phospholipid-bound EPA or DHA, or any combination of the two types of sources.

The source of fat preferably provides docosahexaenoic acid (DHA). In a liquid or gelled composition, a preferred concentration of DHA is between 0.10 and 0.50 g/100 ml.

Micronutrients

Calcium is an important mineral for infants, children and adults. The daily recommended intake ranges from 200 to 800 mg/day for infant and 600-1200 mg/day for adults. It plays an important role in the metabolism and is therefore an essential ingredient in nutritional compositions. Calcium is preferably added to nutritional products as a lactate or phosphate salt, in particular a dicalcium phosphate salt.

The invention in particular pertains to the following preferred embodiments:

1. An enteral nutritional composition with improved taste comprising as free amino acids 0-10 g phenylalanine, 4-8 g valine, 2.5-11 g threonine, 0.7-3 g tryptophan, 2.5-6 g isoleucine, 1.5-4 g methionine, 6.5-8.5 g leucine, 3-6 g lysine, and 1.5-3 g histidine, per 100 g free amino acids in the composition.

2. The composition according to embodiment 1, comprising as free amino acids 0-10 g phenylalanine, 4-6.5 g valine, 7-11 g threonine, 0.7-3 g tryptophan, 3.5-6 g isoleucine, 1.5-4 g methionine, 6.5-8.5 g leucine, 3-6 g lysine, and 1.5-3 g histidine, per 100 g free amino acids in the composition.

3. The composition according to embodiment 1 or 2, comprising substantially no phenylalanine, preferably less than 0.5 g phenylalanine per 100 g free amino acids.

4. The composition according to any one of the preceding embodiments, comprising as free amino acids 0-2 g phenylalanine, 4-6 g valine, 7.5-9 g threonine, 0.7-1.5 g tryptophan, 6.5-7.5 g isoleucine, 1.5-2.5 g methionine, 6.5-7.5 g leucine, 3.5-5 g lysine, and 1.5-2.5 g histidine, per 100 g free amino acids in the composition.

5. The composition according to any of the preceding embodiments, wherein the sum of the amount of free amino acids selected from the group consisting of arginine, aspartic acid, asparagine, histidine, isoleucine, leucine, lysine and methionine is less than 45 wt %, more preferably ranging between 20 and 45 wt %, more preferably between 25 and 40 wt %, most preferably between 30 and 35 wt %, based on the total free amino acids in the composition.

6. The composition according to any of the preceding embodiments, wherein at least 80 wt %, preferably at least 85 wt %, more preferably at least 90 wt % of the proteinaceous matter comprised in the composition is formed from free amino acids.

7. The composition according to any of the preceding embodiments, wherein the weight ratio of the sum of the free amino acids selected from the group consisting of alanine, cysteine (preferably as cystine), glutamine, glutamic acid, proline, serine, threonine and tyrosine to the sum of the free amino acids selected from the group consisting of arginine, aspartic acid, asparagine, histidine, isoleucine, leucine, lysine methionine, tryptophan and valine in the composition ranges between 60:40 and 75:25, more preferably 65:35 and 70:30, most preferably around 2:1.

8. The composition according to any of the preceding embodiments, wherein said composition comprises about 13 g alanine, about 6 g arginine, about 1 g of the sum of aspartic acid and asparagine, about 6 g cystine, about 10 g of the sum of glutamic acid and glutamine, about 12 g glycine, about 2 g histidine, about 4 g isoleucine, about 7 g leucine, about 4 g lysine, about 2 g methionine, about 7 g proline, about 3 g serine, about 8 g threonine, about 1 g tryptophan, about 9 g tyrosine, and about 5 g valine, per 100 g free amino acids, including a 20% weight variation, more preferably a 10% weight variation, most preferably a 5% weight variation in the amount of the individual amino acids, independently.

9. The composition according to embodiment 6, allowing for a maximum deviation of ±0.2, more preferably ±0.1 g in the amounts of amino acids independently.

10. A composition comprising up to 75 wt % GMP, based on the weight of all proteinaceous matter, said composition comprising 0-10 g phenylalanine, 4-8 g valine, 2.5-12 g threonine, 0.7-3 g tryptophan, 2.5-6 g isoleucine, 2-4 g methionine, 6.5-8.5 g leucine, 5-7 g lysine, and 2-3 g histidine, expressed per 100 g protein equivalent in the composition, all as free amino acids, per 100 g proteinaceous material in the composition.

11. The composition according to embodiment 10, comprising 0-10 g phenylalanine, 4-6.5 g valine, 8-12 g threonine, 0.7-3 g tryptophan, 3.5-6 g isoleucine, 2-4 g methionine, 6.5-8.5 g leucine, 5-7 g lysine, and 2-3 g histidine, all as free amino acids, per 100 g proteinaceous material in the composition.

12. The composition according to any of the preceding embodiments wherein the composition further comprises digestible carbohydrates, preferably polysaccharides selected from the group consisting of starch and maltodextrin, and a mixture thereof.

13. The composition according to any of the preceding embodiments for use in the treatment of a subject suffering from a disorder selected from the group consisting of phenylketonuria, homocystinuria, maple syrup urine disease, tyrosinaemia, propionic acidaemia, methylmalonic acidaemia, isovaleric acidaemia, urea cycle disorders and glutaric aciduria.

14. Use of the composition according to any of embodiments 1-13 in manufacture of a product for the treatment of a subject suffering from a disorder selected from the group consisting of phenylketonuria, homocystinuria, maple syrup urine disease, tyrosinaemia, propionic acidaemia, methylmalonic acidaemia, isovaleric acidaemia, urea cycle disorders and glutaric aciduria.

15. A method for feeding a subject, comprising enterally administering to said subject a composition according to any of embodiments 1-13.

16. A method for dietary or nutritional management or treatment of a subject, and/or preventing, treating or reducing the risk of developing a neurological disorder in a subject, comprising enterally administering to said subject a composition according to any of embodiments 1-13.

17. The method according to embodiment 15 or 16, wherein said subject suffers from a metabolic disorder selected from the group consisting of phenylketonuria, homocystinuria, maple syrup urine disease, tyrosinaemia, propionic acidaemia, methylmalonic acidaemia, isovaleric acidaemia, urea cycle disorders and glutaric aciduria, particularly phenylketonuria.

18. A method for improving nutritional status, gut health, stimulating catch-up growth in children suffering from a metabolic disease selected from the group consisting of phenylketonuria, homocystinuria, maple syrup urine disease, tyrosinaemia, propionic acidaemia, methylmalonic acidaemia, isovaleric acidaemia, urea cycle disorders and glutaric aciduria, comprising enterally administering to said children a composition according to any of embodiments 1-13.

19. An enteral nutritional composition with improved taste comprising 0-10 g phenylalanine, 4-8 g valine, 2.5-12 g threonine, 0.7-3 g tryptophan, 2.5-6 g isoleucine, 2-4 g methionine, 6.5-8.5 g leucine, 5-7 g lysine, and 2-3 g histidine, expressed per 100 g protein equivalent in the composition.

20. The composition according to embodiment 19, comprising as free amino acid 0-10 g phenylalanine, 4-6.5 g valine, 8-12 g threonine, 0.7-3 g tryptophan, 3.5-6 g isoleucine, 2-4 g methionine, 6.5-8.5 g leucine, 5-7 g lysine, and 2-3 g histidine, expressed per 100 g protein equivalent in the composition.

21. The composition according to embodiment 19 or 20, comprising substantially no phenylalanine, preferably less than 0.5 g phenylalanine, expressed per 100 g protein equivalent in the composition.

22. The composition according to embodiment 19, 20 or 21, comprising 0-2 g phenylalanine, 5-6.5 g valine, 8.5-10 g threonine, 1-2 g tryptophan, 4-6 g isoleucine, 2-3 g methionine, 7.5-8.5 g leucine, 6-7 g lysine, and 2-3 g histidine, expressed per 100 g protein equivalent in the composition.

EXAMPLES

Comparative Example 1. Amino Acid Composition of the Product According to the Invention Compared to Prior Art Products Table 1 shows the amino acid compositions of products for the dietary management of PKU patients. A product called 'ANC Phenylade' is the prior art product that comes in terms of amino acid composition when compared to the product of the invention, and both are assessed in terms of taste in example 2.

Comparative Example 2. ANC Phenylade and XpheKid vs. Product of the Invention: Taste Perception A non-forced paired preference test of ANC phenylade vs. the amino acid blend according to the invention (preference test 1) and XpheKid vs. the amino acid blend according to the invention (preference test 2) showed clear preference for the composition according to the present invention:

Non-forced paired preference test were performed according to standard methods, as is described in chapter 13, page 303-320 entitled: Preference testing, from the book "*Sensory evaluation of food: Principles and Practices*" 2nd edition, Springer Science+Business Meia LLC2010, from Lawless, H. T. and Heymann H. ISBN 978-1-4419-6487-8

In a non forced paired preference study, two products were presented to the participants simultaneously. All participants were healthy adults. The participants were asked to indicate which of the two products he/she prefers, with the option to express a "no preference". Products were presented blind with a 3 digit number. The order of presentation was balanced. Half of the participants started with test 1 while the other half started with test 2.

The statistical analysis was done as follow for preference test 1: From the 57 participants, 10 expressed a "no preference". Those 10 participants were discounted. On the 47 remaining answers, the two-tailed binomial statistics were applied to check the difference of proportion for the preference between the 2 products. At alpha=5%, with 47 answers, the two tailed binomial table indicated that 31 is the minimum value required to reach a significant preference.

Results for Preference Test 1

Among those expressing a preference (N=47), the AA base according to the invention was significantly preferred over the AA base ANC Phenylade at 95% confidence level (see table 2 & figure 1 below).

TABLE 2

Non-forced paired preference test of ANC phenylade vs. the amino acid blend according to the invention

|  | preference | Significant |
| --- | --- | --- |
| AA blend of invention | 35 | yes |
| AA base ANC Phenylade | 12 |  |
| minimum | 31* |  |
| No choice | 10 |  |

The statistical analysis was done as follow for preference test 2: Form the 57 participants, 6 of them expressed a "no preference". Those 6 participants were discounted. On the 51 remaining answers, the two-tailed binomial statistics was applied to check the difference of proportion for the preference between the 2 products. At alpha=5%, with 47 answers, the two tailed binomial table indicate that 31 is the minimum value required to reach a significant preference.

Results for Preference Test 2:

Among those expressing a preference (N=51), the AA base of the invention was significantly preferred over the AA base PKU XpheKid at 95% confidence level (see table 3).

TABLE 3

Non-forced paired preference test of XpheKid vs. the amino acid blend according to the invention

|  | preference | Significant |
|---|---|---|
| AA blend of invention | 41 | yes |
| AA base ANC Phenylade | 10 | |
| minimum | 33* | |
| No choice | 6 | |

TABLE 1

Amino acid composition of prior art products compared to product of the invention

|  | per 10 g Protein Equivalent)* | Current PKU Anamix Jr | P-AM Anamix | Product of the invention** | ANC Pherrylade | PKU Gel (VF) | Xphe Kid (MetaX) | Phenex 2 (Abbott) | Phenylfree 2 (MU) |
|---|---|---|---|---|---|---|---|---|---|
| Alanine | g | 0.44 | 0.43 | 1.71 (1.31) | 0.93 | 0.43 | 0.54 | 0.67 | 0.65 |
| Arginine | g | 0.82 | 0.8 | 0.63 (0.58) | 0.79 | 0.69 | 0.51 | 0.71 | 0.59 |
| Aspartic acid/asparagine | g | 0.76 | 0.74 | 0.15 (0.10) | 1.4 | 1.1 | 1.32 | 0.08 | 0.78 |
| Cystine | g | 0.3 | 0.3 | 0.68 (0.58) | 0.14 | 0.28 | 0.19 | 0.1 | 0.15 |
| Glutamic acid Glutamine | g | 1.33 | 1.29 | 1.21 (1.01) | 1.55 | 0.85 | 1.44 | 0.14 | 1.58 |
| Glycine | g | 0.79 | 0.75 | 1.65 (1.20) | 0.61 | 1.09 | 0.89 | 0.67 | 0.36 |
| Histidine | g | 0.46 | 0.45 | 0.25 (0.20) | 0.25 | 0.43 | 0.3 | 0.28 | 0.25 |
| Isoleucine | g | 0.73 | 0.71 | 0.5 (0.40) | 0.42 | 0.75 | 0.63 | 0.72 | 0.7 |
| Leucine | g | 1.25 | 1.21 | 0.81 (0.71) | 0.9 | 1.17 | 1.08 | 1.12 | 1.31 |
| Lysine | g | 0.95 | 0.92 | 0.67 (0.41) | 0.73 | 0.78 | 0.82 | 0.67 | 0.79 |
| Methionine | g | 0.2 | 0.19 | 0.26 (0.21) | 0.24 | 0.21 | 0.2 | 0.2 | 0.22 |
| Phenylalanine | g | 0 | 0 | 0 (0) | 0 | 0 | 0 | 0 | 0 |
| Proline | g | 0.88 | 0.86 | 0.81 (0.71) | 0.61 | 0.78 | 0.96 | 0.96 | 0.78 |
| Serine | g | 0.55 | 0.53 | 0.43 (0.29) | 0.9 | 0.49 | 0.65 | 0.51 | 0.39 |
| Threonine | g | 0.61 | 0.59 | 0.91 (0.81) | 0.46 | 0.76 | 0.55 | 0.47 | 0.45 |
| Tryptophan | g | 0.24 | 0.24 | 0.15 (0.10) | 0.23 | 0.23 | 0.22 | 0.11 | 0.18 |
| Tyrosine | g | 1.09 | 1.06 | 0.96 (0.91) | 1.08 | 1.1 | 0.9 | 1 | 0.99 |
| Valine | g | 0.8 | 0.78 | 0.6 (0.50) | 0.67 | 0.87 | 0.74 | 0.81 | 0.76 |
| Citrulline | g | 0 | 0 | 0 | 0 | 0 | 0 | 0 | 0 |
| Carnitine | mg | 5.95 | 5.95 | 8.67 | 14.4 | 10.9 | 9 | 0 | 0 |
| Taurine | mg | 46.2 | 44.9 | 17.6 | 30 | 30.8 | 10 | 0 | 0 |
| Amount of amino acids ('Group B') (mg) |  | 6.21 | 6.04 | 4.02 | 5.63 | 6.23 | 5.82 | 4.7 | 5.58 |
| Amount of amino acids ('Group A') (mg) |  | 5.99 | 5.81 | 8.36 | 6.28 | 5.78 | 6.12 | 4.52 | 5.35 |
| % (B) |  | 50.9 | 51.0 | 32.5 | 47.3 | 51.9 | 48.7 | 51.0 | 51.1 |
| % (A) |  | 49.1 | 49.0 | 67.5 | 52.7 | 48.1 | 51.3 | 49.0 | 48.9 |

*Protein equivalent means that the amounts of free amino acids is expressed in terms of their weight contribution to protein;
**between brackets the amount of free amino acid given in terms of the total amount of free amino acids in the product.

The invention claimed is:

1. An enteral nutritional composition, comprising up to 75 wt % glycomacropeptide (GMP), based on the weight of all proteinaceous matter, and free amino acids, wherein:
   (a) 50-80 wt % of the weight of total free amino acids in the composition is comprised of the sum of the amounts of free amino acids selected from the group consisting of alanine, cysteine, glutamine, glutamic acid, proline, serine, threonine, and tyrosine; and
   (b) 20-40 wt % of the weight of total free amino acids in the composition is comprised of the sum of the amounts of free amino acids selected from the group consisting of arginine, aspartic acid, asparagine, histidine, isoleucine, lysine, methionine, tryptophan, and valine,
   wherein the composition comprises, as free amino acids, at least 0-10 g phenylalanine, 4-8 g valine, 2.5-11 g threonine, 0.7-3 g tryptophan, 2.5-6 g isoleucine, 1.5-4 g methionine, 6.5-8.5 g leucine, 3-6 g lysine, and 1.5-3 g histidine, per 100 g free amino acids in the composition,
   wherein the sum of the amount of free amino acids selected from the group consisting of arginine, aspartic acid, asparagine, histidine, isoleucine, leucine, lysine and methionine is between 25 and 35 wt %, based on the total free amino acids in the composition.

2. The composition according to claim 1, comprising as free amino acids 0-10 g phenylalanine, 4-6.5 g valine, 7-11 g threonine, 0.7-3 g tryptophan, 3.5-6 g isoleucine, 1.5-4 g methionine, 6.5-8.5 g leucine, 3-6 g lysine, and 1.5-3 g histidine, per 100 g free amino acids in the composition.

3. The composition according to claim 1, comprising as free amino acids 0-2 g phenylalanine, 4-6 g valine, 7.5-9 g threonine, 0.7-1.5 g tryptophan, 6.5-7.5 g isoleucine, 1.5-2.5 g methionine, 6.5-7.5 g leucine, 3.5-5 g lysine, and 1.5-2.5 g histidine, per 100 g free amino acids in the composition.

4. The composition according to claim 1, comprising less than 0.5 g phenylalanine per 100 g free amino acids.

5. The composition according to claim 1, wherein at least 80 wt % of the proteinaceous matter comprised in the composition is formed from free amino acids.

6. The composition according to claim 5, wherein at least 90 wt % of the proteinaceous matter comprised in the composition is formed from free amino acids.

7. The composition according to claim 1, wherein the weight ratio of the sum of the amounts of free amino acids selected from the group consisting of alanine, cysteine, glutamine, glutamic acid, proline, serine, threonine and tyrosine to the sum of the amounts of free amino acids selected from the group consisting of arginine, aspartic acid, asparagine, histidine, isoleucine, leucine, lysine, methionine, tryptophan and valine in the composition ranges between 60:40 and 75:25.

8. The composition according to claim 7, wherein the weight ratio of the sum of the amounts of free amino acids selected from the group consisting of alanine, cysteine, glutamine, glutamic acid, proline, serine, threonine and tyrosine to the sum of the amounts of free amino acids selected from the group consisting of arginine, aspartic acid, asparagine, histidine, isoleucine, leucine, lysine, methionine, tryptophan and valine in the composition ranges between 65:35 and 70:30.

9. The composition according to claim 1, comprising 5-7 g cystine, 10-14 g glycine, 8-10 g tyrosine as free amino acids, per 100 g free amino acids in the composition.

10. The composition according to claim 9, comprising 5.5-6.5 g cystine, 10-14 g glycine, 8-10 g tyrosine as free amino acids, per 100 g free amino acids in the composition.

11. The composition according to claim 1, wherein the composition further comprises digestible carbohydrates.

12. The composition according to 11, wherein the digestible carbohydrates comprise polysaccharides selected from the group consisting of starch, maltodextrin, and a mixture thereof.

13. A method for preventing, treating or reducing the risk of developing a metabolic disorder in a subject, comprising enterally administering to said subject an effective amount of a composition according to claim 1.

14. The method according to claim 13, wherein the subject suffers from a metabolic disorder selected from the group consisting of phenylketonuria, homocystinuria, maple syrup urine disease, tyrosinaemia, propionic acidaemia, methylmalonic acidaemia, isovaleric acidaemia, urea cycle disorders and glutaric aciduria, particularly phenylketonuria.

15. A method for improving gut health, and/or stimulating catch-up growth in a child suffering from a metabolic disease selected from the group consisting of phenylketonuria, homocystinuria, maple syrup urine disease, tyrosinaemia, propionic acidaemia, methylmalonic acidaemia, isovaleric acidaemia, urea cycle disorders and glutaric aciduria, comprising enterally administering to the child an effective amount of a composition according to claim 1.

16. The composition according to claim 1, comprising substantially no phenylalanine in the composition.

17. The composition according to claim 1, which is an infant formula.

18. An enteral nutritional composition, comprising up to 75 wt % glycomacropeptide (GMP), based on the weight of all proteinaceous matter, and as free amino acids about 13 g alanine, about 6 g arginine, about 1 g of the sum of aspartic acid and asparagine, about 6 g cystine, about 10 g of the sum of glutamic acid and glutamine, about 12 g glycine, about 2 g histidine, about 4 g isoleucine, about 7 g leucine, about 4 g lysine, about 2 g methionine, about 7 g proline, about 3 g serine, about 8 g threonine, about 1 g tryptophan, about 9 g tyrosine, and about 5 g valine, per 100 g free amino acids, wherein the term "about" represents a 20% weight variation.

19. An enteral nutritional composition, comprising up to 75 wt % glycomacropeptide (GMP), based on the weight of all proteinaceous matter, and free amino acids, wherein:
  (a) 50-80 wt % of the weight of total free amino acids in the composition is comprised of the sum of the amounts of free amino acids selected from the group consisting of alanine, cysteine, glutamine, glutamic acid, proline, serine, threonine, and tyrosine; and
  (b) 20-40 wt % of the weight of total free amino acids in the composition is comprised of the sum of the amounts of free amino acids selected from the group consisting of arginine, aspartic acid, asparagine, histidine, isoleucine, lysine, methionine, tryptophan, and valine,
  wherein the composition comprises, as free amino acids, at least 0-10 g phenylalanine, 4-8 g valine, 2.5-11 g threonine, 0.7-3 g tryptophan, 2.5-6 g isoleucine, 1.5-4 g methionine, 6.5-8.5 g leucine, 3-6 g lysine, 1.5-3 g histidine, 5-7 g cystine, 10-14 g glycine, and 8-10 g tyrosine, per 100 g free amino acids in the composition.

* * * * *